United States Patent [19]

Tagnon

[11] 4,411,501

[45] Oct. 25, 1983

[54] DEVICE FOR CHECKING THE PHORIA OF AN INDIVIDUAL UNDER CONDITIONS OF CLOSE VISION

[75] Inventor: Luc A. Tagnon, St. Mande, France

[73] Assignee: Essilor International, Creteil, France

[21] Appl. No.: 181,181

[22] Filed: Aug. 22, 1980

[30] Foreign Application Priority Data

Aug. 22, 1979 [FR] France .................. 79 21133

[51] Int. Cl.³ ............................................. A61B 3/02
[52] U.S. Cl. ..................................... 351/202; 351/222
[58] Field of Search ................... 351/5, 8, 17, 21, 202, 351/215, 222, 229; 33/200; 350/110, 111, 530, 535, 565, 132, 133, 141

[56] References Cited

U.S. PATENT DOCUMENTS

| | | | | |
|---|---|---|---|---|
| 2,238,207 | 4/1941 | Ames et al. | ............................. | 351/8 |
| 2,676,588 | 4/1954 | Shamsky | ............................. | 128/76.5 |
| 3,822,932 | 7/1974 | Humphrey | ............................. | 351/17 |

FOREIGN PATENT DOCUMENTS 2228460 12/1974 France .
1134831 11/1968 United Kingdom .

Primary Examiner—R. A. Rosenberger
Attorney, Agent, or Firm—Charles A. Brown

[57] ABSTRACT

This device is associated with spectacles 35 which are intended to be worn by the individual in question and which are equipped with crossed analyzers 36, 37.

It comprises a ruler 10, which carries a scale 11 and can be seen in polarized light corresponding to the analyzer 36, and a ruler 12, which carries a reference mark 13 and can be seen in polarized light corresponding to the analyzer 37, the ruler 12 being mounted so that it can move under control of an operating knob 24, for superposition of the reference mark 13 on a determined division of the scale 11, the corresponding displacement of the ruler 12 being assessed by means of a checking scale 28.

Application to the checking of the phoria of an individual under conditions of close vision.

8 Claims, 1 Drawing Figure

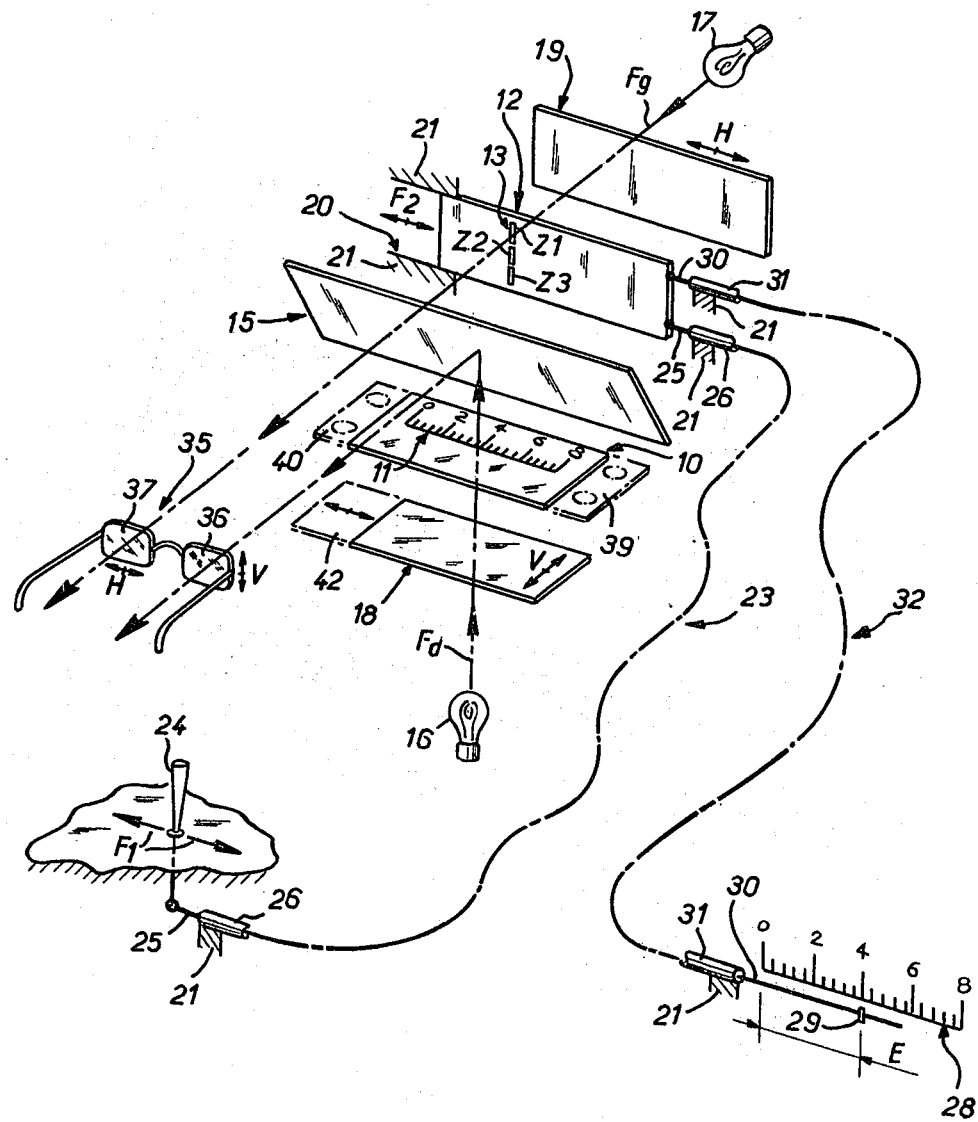

DEVICE FOR CHECKING THE PHORIA OF AN INDIVIDUAL UNDER CONDITIONS OF CLOSE VISION

The present invention relates in general terms to the checking of the phoria of an individual and relates more particularly to the case where this check is to be carried out under conditions of vision at close range, or close vision.

As is known, the phoria of an individual, which is measured in diopters, corresponds to the distance which exists between the observation axes of the eyes of this individual when they are not caused to converge or are caused to converge only slightly.

To make a job ergonomically commensurate with an individual, for example, it is advantageous to be able to check the phoria of this individual.

Hitherto, the phoria of an individual has most frequently been checked in a static manner, that is to say without any intervention by the individual in question, other than the intervention consisting in stating a reading; by virtue of the use of polarized glasses or special lenses, this individual is simultaneously presented with a first test object, which can be observed with one of his eyes, and a second test object, which can be observed with the other eye, and he is asked to read off, against a reference scale, the distance which he sees between these test objects.

Consciously or unconsciously, the individual whose phoria is checked in this way can falsify this reading.

Admittedly, it has already been proposed to check phoria in a non-static manner which involves the displacement of a particular prism interposed in the line of vision of the individual in question.

However, the displacement of this prism is carried out in this case by an operator, and, as previously, the phoria check carried out is based on a reading made by the individual in question.

Thus, hitherto, there has not been any active, or dynamic, participation of the individual in question in the phoria check to which he is subjected.

The present invention relates in general terms to a device which, on the contrary, advantageously involves such participation, which is intended to gain the confidence of the individual in question whilst at the same time making the reading independent of him.

This device, which is thus suitable for checking the phoria of an individual under conditions of close vision, is characterised in general terms in that it comprises, in association with spectacles which are intended to be worn by the individual in question and which are equipped with analysers corresponding to crossed directions of polarization, two observation rulers, namely a first ruler, which carries a scale and can be seen by the said individual in light polarized in a first direction, and a second ruler, which carries a reference mark and can be seen by this individual in light polarized in a second direction crossing the previous direction, either one of the said rulers being mounted so that it can move longitudinally under the control of a governing member at the disposal of the individual in question.

With one of his eyes, the individual whose phoria is to be checked sees the first ruler, namely the one carrying a scale, and with the other eye, he sees the second ruler, namely the one carrying a reference mark, and he is asked, for example, to displace that ruler which is movable, until the reference mark on the second ruler comes opposite a determined division of the scale on the first ruler.

The operator directing the check verifies the displacement made; if it corresponds to the required division, the phoria of the individual in question is zero; in the opposite case, the difference between the required division and the recorded division is a representation of this phoria and can, for example, measure the latter directly in diopters.

However, it is the operator who carries out this measurement and not the individual whose phoria is to be checked, and consequently this measurement can not be influenced in any way, voluntarily or involuntarily, by this individual, who, even if he intended to do so, could not in any way know the supposedly more favorable direction of a deliberate modification, on his part, of the operation which he is asked to carry out.

The measurement carried out is thus totally reliable.

The characteristics and advantages of the invention will moreover become apparent from the description which now follows, by way of example, with reference to the attached schematic drawing, the single FIGURE of which is a perspective representation of the device according to the invention.

In the case of checking the phoria of an individual under conditions of close vision, this device comprises in general terms, and as shown schematically in the figure, two observation rulers, namely a first ruler 10, which longitudinally carries a scale 11 and which, along the path marked by the arrow Fd in the figure, can be seen by the individual in question in light polarized in a first direction, for example a vertical direction V, and a second ruler 12, which carries a reference mark 13 and which, along the path Fg in the figure, can be seen by the said individual in light polarized in a second direction, for example a horizontal direction H, crossing the previous direction.

In the embodiment shown, the ruler 10 is fixed horizontally, directly below a semi-transparent mirror 15, and the ruler 12 is fixed vertically, behind this semi-transparent mirror.

Furthermore, in the embodiment shown, both these rulers 10, 12 are transparent and they are each associated with a light source 16, 17 and a polarizer 18, 19 which, in the case of the ruler 10, corresponds to the direction of polarization V, and in the case of the ruler 12, corresponds to the direction of polarization H, as shown schematically by the double arrows in the figure.

According to the invention, either one of the rulers 10, 12 is mounted so that it can move longitudinally under the control of a governing member at the disposal of the individual in question.

In the embodiment shown, it is the ruler 12 carrying a reference mark 13 which is thus mounted so that it can move.

For example, and as shown schematically in the figure, this ruler 12 can very simply be mounted so that it can slide in a fixed guide 20 forming part of the fixed frame 21 of the device, and can be coupled, by means of a transmission system 23 of the type known by the name "BOWDEN", to an operating knob 24 at the disposal of the user.

As is known, a transmission system of the "BOWDEN" type is a transmission system with a cable 25 and a fixed sheath 26.

At one of its ends, the cable 25 of this transmission system is joined to the ruler 12, and at the other end, it is joined to the operating knob 24.

As regards the sheath 26, it is fixed at each of its ends to the frame 21.

This frame 21 will not be described in full detail in this text because it does not itself form a subject of the present invention and depends on those skilled in the art.

The figure schematically shows only part of this frame, namely only those of its constituent parts which are capable of making the invention easier to understand.

As is easily understood, when the operating knob 24, which is mounted so that it can pivot for this purpose on the frame 21, is tilted from right to left, and vice versa, in the direction of the arrows F1 in the figure, the ruler 12 is controlled with a reciprocating movement in its guide 20, in the direction of the arrows F2.

A checking scale 28, at the disposal of an operator, is associated with the ruler 12.

This checking scale 28, which cannot be seen by the individual whose phoria is to be checked, is a representation of the scale 11 on the ruler 10.

It can be graduated directly in diopters.

A pointer 29, the movement of which is linked to that of the ruler 12, is mounted so that it can move, at right-angles to this checking scale 28.

For example, and as shown, one of the ends of the cable 30, with a fixed sheath 31, of a transmission system 32 of the "BOWDEN" type can be joined to this ruler 12, the other end of this cable 30 carrying the pointer 29.

In the embodiment shown, the reference mark 13 carried by the ruler 12 extends transversely relative to the longitudinal direction of displacement of this ruler, and is divided up into several separate zones; in the embodiment shown, it thus comprises three aligned zones Z1, Z2, Z3.

Spectacles 35, which are intended to be worn by the individual whose phoria is to be checked, are associated with the device according to the invention.

These spectacles are equipped with analysers corresponding to crossed directions of polarization.

For example, for the right eye, the analyser 36 in question corresponds to the direction of polarization V, and for the left eye, the analyser 37 in question corresponds to the direction of polarization H, as shown schematically by double arrows in the figure.

A phoria check using the device according to the invention is carried out in the following manner.

The individual whose phoria is to be checked is equipped with the spectacles 35 and, in a first stage, darkness is created so that this individual cannot see anything and so that his eyes relax.

The light sources 16, 17 are then switched on. Thereafter, the individual in question sees the scale 11 on the ruler 10 with his right eye and the reference mark 13 on the ruler 12 with his left eye.

He is then asked to bring this reference mark 13 into coincidence with a determined division of the scale 11.

To do this, he must control the displacement of the ruler 12, using the operating knob 24, until the required superposition is obtained.

The pointer 29 moves conjointly opposite the checking scale 28, as a representation of the displacement of the ruler 12.

If the individual in question does not suffer from phoria, that division of the checking scale 28 opposite which the pointer 29 is positioned corresponds to the required division.

The same does not apply in the opposite case, and the corresponding distance is a measurement of the phoria of the individual in question.

The operator directing the checking of this phoria records this distance directly; the distance can be measured directly in diopters.

To illustrate the invention, it has been assumed, in the figure, that the division of the scale 11 on which the individual in question has been asked to superpose the reference mark 13 is the division O, and that this individual has a phoria of four diopters, taking account of the distance E existing between the pointer 29 and the division O of the checking scale 28.

Conjointly, the individual in question can be asked to specify which of the zones Z1, Z2, Z3 of the reference mark 13 is cut by the base line of the scale 11 in the view which he has of the whole arrangement, and this makes it possible to assess the possible vertical phoria of this individual, the previous measurement actually relating only to his horizontal phoria.

As shown schematically in broken lines in the figure, the ruler 12 can also carry, at its ends, a test object 39, which can be seen in light polarized in the direction V, in the same way as the scale 11, and, on the other side, a test object 40, which is identical to the previous test object but which can be seen in light polarized in the direction H crossing the previous direction, a polarizer 42, corresponding to this direction, laterally extending the polarizer 18 for this purpose.

For example, the test objects 39, 40 can each be formed of two elements which are respectively red and green in colour.

By asking the individual in question which of these elements he sees more clearly, it is possible to assess whether he is hypermetropic or myopic.

In all cases, it will be appreciated that the device according to the invention advantageously does not involve the interposition, in the view of the individual in question, of any optical element, other than simple analysers, which is capable of modifying and hence of perturbing the normal conditions of observation of this individual.

Of course, the present invention is not limited to the embodiment which has been described and shown, but encompasses any modified embodiment.

In particular, the movable ruler could equally well be the only ruler carrying a scale, and/or be movable not only longitudinally, in order to assess the horizontal phoria, but also transversely, in order to assess the vertical phoria.

I claim:

1. A phoria testing device comprising a first transparent strip member having a graduated scale thereon and a second transparent strip member having a reference mark thereon, light means capable of generating a light beam which is directed through each of said transparent members towards the eyes of the person to be tested, means for polarizing the beams of light directed through said first and second transparent members in crossed directions, a first means for analyzing light polarized in said first direction and a second means for analyzing light polarized in said second direction being provided for the respective eyes of the person being tested, means slidably mounting one of said transparent members, and operating means controlled by the person being tested for effecting movement of said one slidably mounted member and causing the displacement of said reference mark along said graduated scale to bring said reference mark into alignment with a particular graduation of said graduated scale as viewed by the person being tested, and means responsive to the sliding movement of said one slidably movable member to assimilate the displacement and alignment of said reference mark along and relative to said graduated scale on a second scale remote from said first scale for remote viewing by an operator.

2. The phoria testing device of claim 1, wherein said one slidably mounted member is said second transparent member.

3. The phoria testing device of claim 1, wherein said means mounting said one slidably mounted member comprises a fixed guide in which said one slidably mounted member moves, and Bowden wire means coupled between said one slidably mounted member and said operating means.

4. The phoria testing device of claim 1, wherein said means responsive to the sliding movement of said one slidably movable member comprises a second Bowden wire means connected at one end to said one slidably movable member, the other end carrying an index displaceable along said second remote scale.

5. The phoria testing device of claim 2, wherein said reference mark on said second transparent member extends transversely to the direction of displacement of said first transparent member.

6. The phoria testing device according to claim 1, wherein said other transparent member is fixed, a first test object located at one end of said fixed transparent member and being visible in the light beam polarized in said first direction and a second identical test object located at the other end of said fixed transparent member and being visible in the light beam polarized in said second direction.

7. The phoria device according to claim 6, wherein said first and second test objects are respectively red and green in color.

8. The phoria testing device according to claim 1, wherein said first and second means for analyzing polarized light are mounted in an eyeglass frame.

* * * * *